US005728858A

United States Patent [19]

Lewis et al.

[11] Patent Number: 5,728,858
[45] Date of Patent: Mar. 17, 1998

[54] ACTIVATION OF COPPER-SILICON SLURRIES FOR THE DIRECT SYNTHESIS OF TRIALKOXYSILANES

[75] Inventors: Kenrick M. Lewis, Rego Park; Hua Yu, White Plains, both of N.Y.

[73] Assignee: OSi Specialties, Inc., Greenwich, Conn.

[21] Appl. No.: 728,228

[22] Filed: Oct. 10, 1996

[51] Int. Cl.⁶ .................................. C07F 7/18; C07F 7/04
[52] U.S. Cl. .......................................................... 556/470
[58] Field of Search ................................................ 556/470

[56] References Cited

U.S. PATENT DOCUMENTS 4,487,949  12/1984  Mallon ................................ 556/470
4,762,939  8/1988  Mendicino ........................... 556/470
4,931,578  6/1990  Ohta et al. .......................... 556/470

*Primary Examiner*—Paul F. Shaver
*Attorney, Agent, or Firm*—Scully, Scott, Murphy & Presser

[57] ABSTRACT

Disclosed is an improved process for the slurry phase Direct Synthesis of trialkoxysilanes which comprises the activation of copper catalyst and silicon with a reducing agent such as hydrogen gas, carbon monoxide or monosilane. Such activation affords high, stable reaction rates and selectivities and high silicon overall conversion especially in alkylated benzene solvents.

15 Claims, 7 Drawing Sheets

ACTIVATION OF COPPER-SILICON SLURRIES FOR THE DIRECT SYNTHESIS OF TRIALKOXYSILANES

FIELD OF THE INVENTION

The invention relates to the production of trialkoxysilanes in the catalyzed reaction of silicon metal with alcohols. In particular, the process entails the activation of silicon metal with halogen free catalyst precursors such as copper (II) hydroxide in the presence of hydrogen, carbon monoxide, monosilane and other reducing agents prior to the reaction with the alcohol. The process exhibits a high selectivity for trialkoxysilane, a high overall silicon conversion and a high reaction rate.

BACKGROUND OF THE INVENTION

Trialkoxysilanes, especially trimethoxysilane and triethoxysilane, are used in the production of silane coupling agents. One method of synthesis of trialkoxysilanes is directly from silicon and an alcohol. This method is known variously in the art as the Direct Synthesis, the Direct Reaction, the Direct Process or the Rochow Reaction. For trialkoxysilanes, it is most conveniently performed in slurry reactors.

In a slurry reactor for the Direct Synthesis of trialkoxysilanes, catalytically-activated silicon particles are maintained in suspension in a thermally stable, high boiling solvent and are made to react with an alcohol at an elevated temperature. This type of reaction is disclosed by Rochow in U.S. Pat. No. 3,641,077. The patent teaches preparation of trialkoxysilanes by directly reacting copper-silicon mass, suspended in a silicone oil, with alcohol at 250°–300° C. The copper-silicon mass contains about 10 weight percent copper and is prepared by heating copper and silicon above 1000° C. in a furnace in a stream of hydrogen gas. This method results in low yields of trialkoxysilanes.

U.S. Pat. No. 3,775,457 teaches the use of polyaromatic hydrocarbon oils as solvents in the Direct Synthesis of trialkoxysilanes from an alcohol and finely divided silicon metal activated with cuprous chloride catalyst. Although the use of cuprous chloride results in increased yield over that obtained using the sintered copper-silicon mass of U.S. Pat. No. 3,641,077, the use of cuprous chloride catalyst also results in the formation of HCl which, in turn, necessitates the use of costly corrosion resistant materials of construction for the reactor and its ancillary equipment. Further, the presence of chloride in the reactor and in the product stream reduces the yield of trialkoxysilane by catalyzing the consecutive reaction of trialkoxysilane with the alcohol to yield tetraalkoxysilanes.

Additionally, when methanol is a reactant, such as to produce trimethoxysilane, the HCl resulting from the use of the cuprous chloride catalyst will react with some of the methanol to produce methyl chloride and water. This loss of methanol to an undesirable side reaction makes the cuprous chloride catalyzed reaction inefficient. Moreover, water produced by this reaction can react with trialkoxysilanes and tetraalkoxysilanes to produce soluble and gelled siloxanes and further reduce the efficiency of the Direct Process. The presence of water in the reaction mixture can also inhibit the sustained conversion of silicon metal to desirable products at economically beneficial rates. Other patents, for example Japenese Kokai Tokkyo Koho 55-28928 (1980), 55-28929 (1980), 55-76891 (1980), 57-108094 (1982) and 62-96433 (1987), which disclose the use of cuprous chloride or cupric chloride and alkylated benzene solvents such as dodecylbenzene and tridecylbenzene, are subject to these same limitations. It is desirable to use the alkylated benzenes because they are less expensive and less hazardous to people and the environment than the polyaromatic hydrocarbon solvents of U.S. Pat. No. 3,775,457.

U.S. Pat. No. 4,727,173 discloses that the use of copper (II) hydroxide as catalyst avoids the limitations associated with cuprous chloride and provides a high selectivity to trialkoxysilanes. The preferred solvents are diphenyl ether, polyaromatic hydrocarbons like THERMINOL® 59, THERMINOL® 60 and THERMINOL® 66, and alkylated benzenes such as dodecylbenzene. However, when copper (II) hydroxide is used in combination with alkylated benzene solvents, such as dodecylbenzene, the Direct Synthesis of trialkoxysilanes becomes unstable after approximately 25–35 weight percent of the silicon has been reacted. When methanol is the alcohol reactant at temperatures above about 220° C., the trimethoxysilane content in the reaction product declines from approximately 90–95 weight percent to approximately 50–60 weight percent and recovers again to between 80–95 weight percent after about 60 percent silicon conversion. Simultaneous with this loss of selectivity is the enhanced formation of methane, water and dimethyl ether. Methane and dimethyl ether formation represent inefficient use of the methanol reagent. Problems attendant to the generation of water in the reaction mixture have been recited hereinabove.

Alcohol dehydration and dehydrogenation are especially troublesome problems when ethanol and other higher homologs are used in the Direct Synthesis. At some temperatures ( >250° C.), alkenes and aldehydes, and not the desired trialkoxysilanes, are formed in significant amounts. Even when these are not the predominant products, their presence in the reaction mixture can result in the inhibition of further catalytic activity. At lower temperatures, (for example 220° C.) alcohol decomposition reactions are less prevalent, but the Direct Synthesis is impractically slow. Japanese Kokai Tokkyo Koho 55-2641 (1980) discloses the use of cyclic ethers to improve reactivity and selectivity to triethoxysilane when the Direct Synthesis is conducted in dodecylbenzene at these lower temperatures. Cyclic ethers such as dibenzo-18-crown-6 are quite expensive; others such as 12-crown-4 are also toxic.

U.S. Pat. No. 5,527,937 (European Patent application EP 0709388 A1) discloses a process for the Direct Synthesis of triethoxysilane, wherein CuCl is the catalyst, tri- and tetratoluenes and/or their alkyl substituted derivatives are the solvents and dimethylsilicone oils are antifoaming agents. The polyphenyl solvents of this process are expensive heat transfer fluids.

The use of hydrogen to activate silicon with copper for the Direct Reaction has been disclosed in U.S. Pat. Nos. 2,380,997; 2,473,260; 3,641,077; and 4,314,908. Hydrogen activation, as taught in these patents, is accomplished at temperatures above about 400° C. in fixed bed reactors, fluidized bed reactors or furnaces with silicon-copper catalyst mixtures containing more than 1.5 weight percent copper. No teaching is given regarding selectivity, reactivity and reaction stability of the silicon-copper masses in the slurry phase Direct Synthesis of trialkoxysilanes.

Suzuki, et al. (Bulletin of the Chemical Society of Japan, vol. 64 (1991) pp 3445–3447) disclosed that hydrogen activation of silicon-$CuCl_2$ mixtures (2.5 wt % Cu) in a fixed bed at 260° C. afforded complete silicon conversion and high (89%) selectivity to trimethoxysilane in a fixed bed Direct Reaction with methanol. The duration of the induction period, the reaction rate and selectivity to trimethoxysilane were all very dependent on the temperature of hydrogen activation.

Thus, there continues to exist the need for a stable, highly selective and rapid Direct Synthesis of trialkoxysilanes which is conducted in cheaper, less hazardous solvents and yet avoids the above-mentioned deficiencies of copper chlorides and alkylated benzenes. In particular, there is a need for such a Direct Synthesis which eliminates or avoids the alcohol reduction, alcohol dehydration and alcohol dehydrogenation side reactions.

OBJECTS OF THE INVENTION

It is therefore an object of the invention to provide a process for producing trialkoxysilane from silicon metal and alcohol which results in a high trialkoxysilane to tetraalkoxysilane ratio in the product over the entire course of the reaction.

Another object of the invention is to provide such a process for use in alkylated benzene solvents while avoiding significant alcohol reduction, dehydrogenation and dehydration and formation of silicate gels, hydrocarbons, water and dialkyl ethers.

Another object of the invention is to provide such a process which results in a high conversion of silicon metal into trialkoxysilane product and which results in little unreacted silicon content in the solid reaction residue.

A further object of the invention is to provide such a process which uses raw materials that are substantially free of halides and other corrodents and which does not require the use of costly corrosion resistant materials in the construction of the process apparatus.

SUMMARY OF THE INVENTION

The present invention provides a process for producing trialkoxysilane of the formula, $HSi(OR)_3$, wherein R is an alkyl group containing from 1 to 6 carbon atoms inclusive, which process comprises:

(a) slurrying silicon metal in a thermally stable solvent in the presence of a catalyst precursor which is halogen-free and which comprises copper at least part of which is not in the Cu° state and is reducible to the Cu° state, (b) fully reducing said copper which is not in the Cu° state to the Cu° state, thereby generating a catalyst for the reaction of step (c), and (c) reacting said silicon metal with an alcohol of the formula ROH in the presence of the catalyst generated in step (b) to form said trialkoxysilane.

A preferred mode of carrying out this process comprises (a) forming a reaction mixture comprising a thermally stable solvent, preferably an alkylated benzene solvent or polyaromatic hydrocarbon solvent, silicon metal, a catalytically effective amount of copper or a copper compound not containing halogens, preferably copper (II) hydroxide, and optionally an alcohol of formula ROH;

(b) agitating this mixture and injecting into it hydrogen, or reducing gases containing hydrogen, under conditions sufficient to effect the reduction of Cu(II) and/or Cu(I) to the fully reduced valence states;

(c) reacting the copper-activated silicon so formed with an alcohol of the formula ROH to produce trialkoxysilane; and (d) recovering said trialkoxysilane from the reaction product.

The process of the present invention prevents significant silicate gel, hydrocarbon, water and dialkyl ether formation and affords good reaction stability in alkylated benzene and polyaromatic hydrocarbon solvents. The process produces trialkoxysilanes at high rates and in quantity such that the gravimetric ratios of trialkoxysilane to tetraalkoxysilanes are greater than about 9 to 1 when measured over the entire course of a reaction. Furthermore, the use of the preferred catalyst precursor, copper (II) hydroxide, and hydrogen does not generate corrosive materials, and thus costly materials of construction are not required for the reactor. The process of this invention also results in high overall conversion of silicon and alcohol to desirable products.

DETAILED DESCRIPTION OF THE INVENTION

Figure 1:
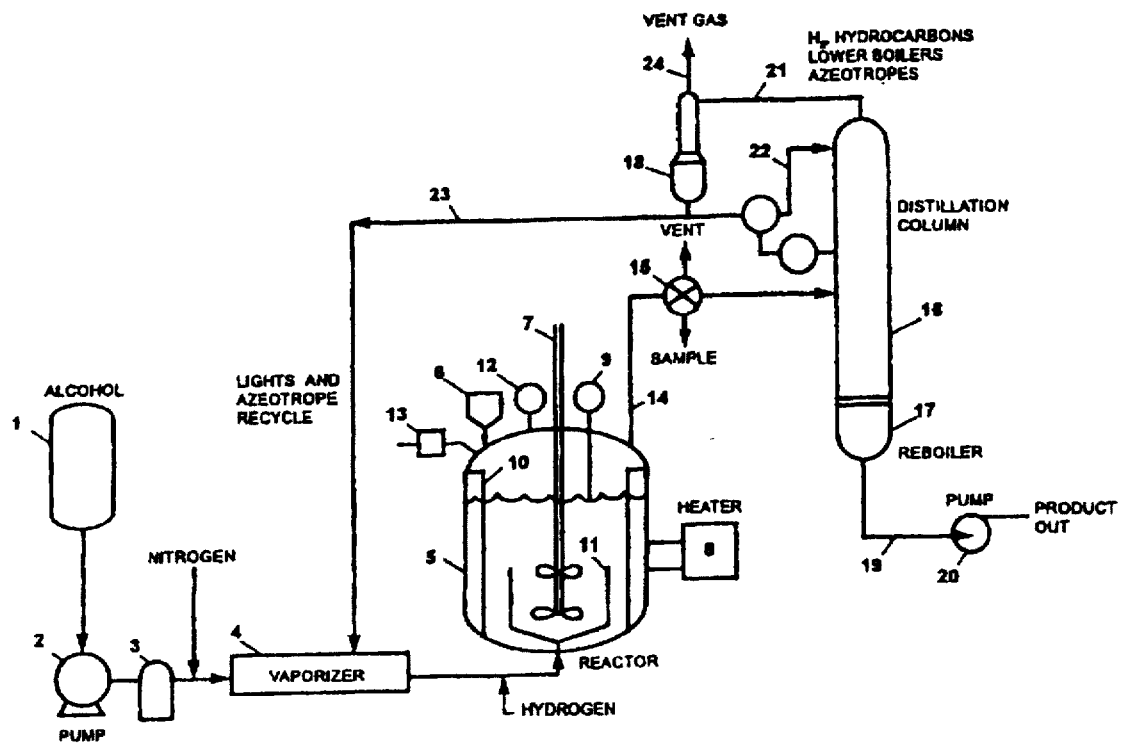
FIG. 1 is a schematic drawing of the slurry reaction apparatus for the direct synthesis of trialkoxysilanes.

The following equations are representations of the principal chemical reactions occurring during the Direct Synthesis of trialkoxysilanes:

| | |
|---|---|
| $Si + 3ROH \rightarrow HSi(OR)_3 + H_2$ | (1) |
| $HSi(OR)_3 + ROH \rightarrow Si(OR)_4 + H_2$ | (2) |
| $ROH + H_2 \rightarrow RH + H_2O$ | (3) |
| $2ROH \rightarrow ROR + H_2O$ | (4) |
| $RCH_2OH \rightarrow R'CH=CH_2 + H_2O$ | (5) |
| $2Si(OR)_4 + H_2O \rightarrow (RO)_3SiOSi(OR)_3 + 2ROH$ | (6) |
| $2HSi(OR)_3 + H_2O \rightarrow H(RO)_2SiOSi(OR)_2H + 2ROH$ | (7) |
| $2HSi(OR)_3 + Si(OR)_4 + H_2O \rightarrow$ $HSi(RO)_2OSiOSi(OR)_2OSi(OR)_2H + 2ROH$ | (8) |

The desirable products of the instant Direct Synthesis are trialkoxysilanes of general formula, $HSi(OR)_3$, wherein R is an alkyl group of 1 to 6 carbon atoms. R is preferably methyl or ethyl. Byproducts of the synthesis are $Si(OR)_4$, $RSiH(OR)_2$, $RSi(OR)_3$, linear, branched and cyclic silicates such as $(RO)_3SiOSi(OR)_3$, $H(RO)_2SiOSi(OR)_2H$, $HSi(RO)_2SiOSi(OR)_3$, $(RO)_3SiOSi(OR)_2R$, $(RO)_3SiOSi(RO)_2OSi(RO)_3$, $(RO)_3SiOSi(OR)HOSi(OR)_3$, $(RO)_3SiOSi(OR)ROSi(OR)_3$, $(RO)_3Si[OSi(OR)_3]_3$, $(RO)_3SiOSi(OR)(OSi(RO)_3)OSi(OR)_3$, and $[OSi(OR)_2]_n$, (n=3, 4, 5 . . . ), hydrogen gas, hydrocarbons (RH) such as methane and ethane, alkenes ($R'CH=CH_2$) such as ethylene and ethers (ROR) such as dimethyl ether and diethyl ether. In the general formula, R'CH=CH$_2$, for the alkene byproducts. R' is hydrogen or an alkyl group of 1 to 4 carbon atoms. Hydrogen gas, hydrocarbons and the ethers are typically not condensed in the cold trap with the liquid products and exit the apparatus as a gaseous stream. Some of the silicates are volatilized out of the reactor and are soluble in the liquid reaction product. Others remain solubilized in the solvent or precipitate as insoluble gels.

When the Direct Synthesis is conducted pursuant to the present invention, trialkoxysilanes comprise at least 80 weight percent, preferably at least 85 weight percent, of the liquid reaction products. Typical levels of the alkyl silicates, Si(OR)$_4$, are less than 9 weight percent, preferably less than 6 weight percent. RSiH(OR)$_2$ and RSi(OR)$_3$ compounds are individually less than 2 weight percent and preferably less than 1 weight percent. Condensed silicates are maximally 1 weight percent and preferably less than 0.5 weight percent. In addition to the percentage ranges taught hereinabove, selectivity to the desired trialkoxysilanes may also be expressed as the gravimetric ratio, HSi(OR)$_3$/Si(OR)$_4$. By the method of the instant invention, this ratio is at least 9 when computed over the total course of a reaction. It is preferably at least 15 and may attain values greater than 30 during the steady-state portion of the reaction.

Gas chromatographic (GC) analysis has been found to be a reliable and accurate technique to quantify the composition of the liquid reaction product. Other methods such as nuclear magnetic resonance (NMR) and mass spectrometry (MS) may also be used. These are particularly useful for identifying and quantifying the higher molecular weight silicates contained in the reaction product and reaction solvent. Data on the composition and weight of the reaction product and the fraction of silicon in each of the components are used to calculate the silicon conversion. Reaction rate is typically expressed as silicon conversion per unit time.

In the nomenclature of silicon chemistry, silicon atoms bonded to four oxygen atoms are designated Q groups. Q$^0$ represents the monomers, Si(OR)$_4$. Q$^1$ designates the groups, OSi(OR)$_3$, at the ends of chains; Q$^2$ denotes internal groups, OSi(OR)$_2$O, in chains or cyclics; Q$^3$ refers to branching sites, OSiO(OR)O, and Q$^4$ to fully crosslinked groups, Si(OSi)$_4$. These groups have characteristic $^{29}$Si NMR chemical shifts within the range, −70 to −120 ppm whose assignments are facilitated by the use of DEPT (distortionless enhancement of polarization transfer) and depth pulse analysis. Publications by Brunet, et. al. (Journal of Physical Chemistry, vol. 95 (1991), pp 945–951; Journal of Non-Crystalline Solids, vol. 163 (1993) pp 211–225) and Bendall, et al. (Journal of Magnetic Resonance, vol. 53 (1983) 365–385) detail the use of these NMR analytical techniques.

The gaseous product stream contains hydrogen gas, hydrocarbons, ethers and inert agents such as nitrogen or argon. Analytical methods based on gas chromatography, Fourier Transform Infra-red spectroscopy (FTIR) or mass spectrometry may be used to identify and quantify these components in the gaseous effluent. Assuming that the reaction of Equation 1 produces most of the hydrogen gas in the effluent, the hydrogen generated in the Direct Synthesis can be used as an approximate measure of reaction rate and silicon conversion. Hydrocarbon and ether formation depicted in Equations 3–5 can be used as a measure of the inefficiency of alcohol conversion. It is desirable that less than 2 weight percent of the alcohol fed to the reaction be converted to hydrocarbons and ethers and most desirable than none be so converted.

Gravimetry and atomic absorption spectroscopy are suitable methods for quantifying the silicon content of the reaction solvent. Analytical procedures are published, for example, in The Analytical Chemistry of Silicones, (A. L. Smith, Editor), John Wiley & Sons Inc., New York, 1991, chapter 8. Soluble silicates retained in the reaction solvent are a measure of the extent to which side reactions such as those in Equations 6–8 have occurred. All of these reactions depend on the presence of water, which is formed, for example, by the reactions of Equations 3–5. Gels and soluble silicates contained in the reaction solvent can be removed with boric acid and borates according to the method disclosed by Bailey, et al. in U.S. Pat. No. 5,166,384, which is hereby incorporated herein by reference.

CATALYST PRECURSORS

Copper and halogen-free copper compounds which are readily reducible to copper (i.e., Cu°) by hydrogen, alcohols, hydridoalkoxysilanes and other organosilanes containing SiH, SiH$_2$ or SiH$_3$ groups, monosilane (SiH$_4$), carbon monoxide and/or by heating, optionally in the presence of the defined solvents of the instant invention, are the precursors i.e. the starting materials, for production of catalysts used in this inventive process. Suitable examples are metallic copper powders, including those produced by supercritical processes, metal atom vaporization or in situ in the reaction mixture, copper colloids, copper oxides, copper hydroxides, mixed hydrous oxides such as 3CuO.Cu(OH)$_2$, copper alkoxides (typically of the formula (Cu(OA)$_{1-2}$ wherein A is straight or branched C$_{1-6}$ alkyl, for example, Cu(OCH$_3$)$_2$, Cu(O-tC$_4$H$_9$)) and carboxylates (typically of the formula Cu(OOA)$_{1-2}$ wherein A is as defined herein, for example, Cu(OOCH)$_2$, Cu(OOCCH$_3$)$_2$). All polymorphic forms of copper (II) hydroxide, particularly the cubic and orthorhombic polymorphs, are preferred catalyst precursors of the instant invention.

The copper catalyst precursor used in the process of this invention is present in an amount effective to catalyze the reaction following the reduction of the catalyst precursor as taught herein. Generally an effective amount ranges from about 0.01 to about 5 parts by weight of catalyst per 100 parts by weight of the silicon metal. Usually the amount of catalyst precursor, such as copper (II) hydroxide, will be from about 0.1 to about 2.6 parts by weight per 100 parts by of the weight silicon metal. The preferred amount of copper catalyst precursor is from about 0.1 to about 1.0 parts by weight per 100 parts by weight silicon metal.

Copper (II) hydroxide used in the present invention is preferably anhydrous, but material containing water of hydration is also usable. The water content of commercial copper (II) hydroxide may be as high as 20 weight percent. If the hydrated catalyst precursor is used, provision must be made in the design of the apparatus to avoid contact of the water formed during its reduction and thermal decomposition with the trialkoxysilane and alkylsilicates contained in the reaction product.

In addition to water content, various other criteria can be used to characterize the copper catalysts and catalyst precursors of this invention. Surface area of the copper (II) hydroxide can be as low as 1 m$^2$/g. Areas in the range 10–50 m$^2$/g are preferred. Particle size of the copper (II) hydroxide can be from less than 1 micron up to about 100 microns. The desirable range is 0.1–50 microns and the preferred range 0.1–30 microns.

The presence of excessive tin in the reaction has adverse effects on the reaction rate and/or the selectivity for trialkoxysilane and so such excessive tin levels should be avoided. It is desirable that the tin content of the catalyst be less than 1000 parts per million, preferable that it be less than 300 parts per million and most preferable that it be less than 100 parts per million. Of greater importance is the tin content of the reaction slurry. Based on the weight of silicon at the outset of a reaction, it is desirable that the tin content be less than 100 parts per million and preferable that it be less than 10 parts per million.

Zinc content of the catalyst is desirably less than 2500 parts per million and preferably less than 1500 parts per million. Based on the initial weight of silicon charged to the reactor, zinc content of the reaction slurry must be less than 100 parts per million, and preferably less than 50 parts per million. Other critical trace elements which are ordinarily contained in the catalyst are lead (Pb) and chloride (Cl$^-$). Their concentrations in the slurry must be <50 parts per million and <100 parts per million, respectively. The chloride restriction arises from its impact on reactor corrosion, not on reaction rate or selectivity. As a practical matter, trace amounts of chloride (up to about 0.1 weight percent) may be present inherently or adventitiously in the catalyst precursor.

SILICON

The silicon metal reactant used in the process of this invention can generally be any commercially available grade of silicon in particulate form. It may be produced by any of the methods in current practice such as casting, water granulation, atomization and acid leaching. These methods are more fully described in *Silicon for the Chemical Industry*, vols. I, II III, (H. Oye, et al, Editors), Tapir Publishers, Norwegian Institute of Technology. A typical composition of commercial silicon metal useful in this invention expressed in percent by weight, is Si ~98.5%, Fe <1%, Al ~0.05 to 0.7%, Ca ~0.001 to 0.1%; Pb <0.001%, Water <0.1%. Generally, smaller particle sizes are preferred for ease of dispersion in the slurry, faster reaction and minimization of erosion in the reactor. Sieving of ground silicon to regulate particle size is optional. An unsieved sample with particle sizes from <45 microns to >600 microns performed as satisfactorily as a sieved one with particle sizes in the narrower range, 75–300 microns.

ALCOHOL

The alcohols which are useful in the process of this invention are those of the formula ROH wherein R is an alkyl group containing from 1 to 6 carbon atoms, inclusive. Preferably R is an alkyl group containing from 1 to 3 carbon atoms inclusive. The most preferred alcohols are methanol and ethanol.

Generally, the reaction is run batchwise in a slurry and the alcohol is fed into the slurry as a gas or liquid. Gaseous introduction is preferred. An induction period lasting from a few minutes up to about five hours may be observed. The initial alcohol feed rate is optionally controlled at a low level and increased following the induction period. Similarly, the alcohol feed rate is optionally reduced after about 70 weight percent silicon conversion to minimize the formation of tetraalkoxysilanes. Generally, once the reaction is running, the alcohol feed rate can be adjusted to give the desired level of alcohol conversion. One skilled in the art can readily adjust the feed rate in a given reaction run by monitoring the product composition. If the feed rate is too high the product stream will contain a larger proportion of unreacted alcohol. It is preferable that the alcohol be anhydrous. However, water contents of up to 0.1 weight percent can be tolerated without significant loss of selectivity, reactivity and stability.

SOLVENT

The solvents useful in the process of this invention are thermally stable solvents that do not degrade under the activation and reaction conditions. The preferred solvents are high temperature stable organic solvents typically used as heat exchange media. Examples include THERMINOL® 59, THERMINOL® 60, THERMINOLI® 66, DOWTHERM® HT, MARLOTHERM® S, MARLOTHERM® L, diphenyl ether, diphenyl, terphenyl and alkylated benzenes, alkylated diphenyls and alkylated terphenyls with normal boiling points higher than about 250° C.

THERMINOL® is the Monsanto Company trade name for heat transfer fluids. THERMINOL® 59 is a mixture of alkyl-substituted aromatic compounds recommended for use between −45° to 315° C. THERMINOL® 60 is a mixture of polyaromatic compounds with an average molecular weight of 250. Its optimum usage temperature is in the range from −45° to 315° C. THERMINOL® 66 and DOWTHERM® HT are mixtures of hydrogenated terphenyls with an average molecular weight of 240. Maximum temperature limit is about 370° C. THERMINOL® 59, THERMINOL® 66 and DOWTHERM® HT are preferred solvents of this invention. DOWTHERM® fluids are produced by Dow Chemical Company.

MARLOTHERM® is the Hüls AG trade name for its heat transfer fluids. MARLOTHERM® S is a mixture of isomeric dibenzylbenzenes. MARLOTHERM® L is a mixture of isomeric benzyl toluenes. Both can be used at temperatures up to about 350° C. Both are preferred solvents for the instant invention.

Suitable alkylated benzenes are dodecylbenzene, tridecylbenzene, tetradecylbenzene and their mixtures such as are sold by Vista Chemical Company under the trade name NALKYLENE®. NALKYLENE® 550BL, NALKYLENE® 550L and NALKYLENE® 600L are particularly preferred solvents of this invention. When activation of the copper (II) hydroxide-silicon mixture is practiced in an alkylated benzene solvent and the resulting slurry reacted with methanol vapor, no loss of selectivity to trimethoxysilane is observed between 25–35 weight percent silicon conversion. Mixtures of alkylated benzenes and polyaromatic hydrocarbons are also useful solvents for the instant invention. Used solvents can be treated with boric acid and borates as described in U.S. Pat. No. 5,166,384 and reused in subsequent reactions.

Silicon metal, catalyst and solvent can be added together in the reactor in any order. The solvent is present in an amount sufficient to disperse the solid and gaseous reactants homogeneously. Generally, reactions are initiated with solvent and solids in a gravimetric ratio between 1:2 and 4:1, preferably 1:1 to 2:1. However, as the silicon is consumed during batchwise Direct Synthesis, the solvent to solids ratio will increase. The ratio can be maintained within narrow limits of the preferred range for continuous reactions.

ACTIVATION CONDITIONS

Activation is the process of incorporating catalyst, and if desired, other auxiliary agents, into the silicon to make it reactive with the alcohol. Activation may be performed in the same reactor used for the Direct Reaction of the alcohol, or in a separate reactor. In the latter case, the activated silicon is typically and desirably transported to the synthesis reactor in an anhydrous, non-oxidizing atmosphere. Transportation of the activated silicon as a slurry in the reaction solvent is especially preferred.

The reductive activation of the present invention is performed between 20°–400° C. preferably between 150°–300° C., with silicon-copper catalyst precursor mixtures containing 0.01–5 weight percent copper, i.e. as the ratio (Cu/(Cu+

Si)). Useful reducing agents include $H_2$, CO, $SiH_4$ and mixtures containing them. $H_2$ is the preferred reducing agent. Activation may be performed with the silicon and copper catalyst precursor in their dried state in fluidized bed or fixed bed reactors. Thereafter, the activated silicon is transported to the slurry reactor for reaction with the alcohol. Alternatively, hydrogen or another reducing agent is introduced into an agitated mixture of silicon and copper catalyst precursor in the presence of the reaction solvent. Preferably, the reducing agent is introduced into an agitated mixture of silicon and copper catalyst precursor in alkylated benzene solvents such as NALKYLENE® 550BL, NALKYLENE®600L or polyaromatic hydrocarbon solvents such as THERMINOL® 59, THERMINOL® 60 or THERMINOL® 66 or MARLOTHERM® S or MARLOTHERM® L or DOWTHERM® HT. Alcohol is optionally present during the activation with hydrogen. The total quantity of reducing agent must be sufficient to bring about effective activation and avoid significant loss of trialkoxysilane selectivity, and/or formation of undesirable byproducts such as hydrocarbons and water during the Direct Synthesis.

Activation of silicon-copper catalyst precursor mixtures with hydrogen can produce water, alcohols, carboxylic acids and other compounds. These compounds are preferably volatilized so that they are absent prior to the start of the Direct Synthesis of the trialkoxysilanes. If they are present in the synthesis reactor or in the product retention vessel, they can contribute to gel formation, poor reaction selectivity and reduced trialkoxysilane recovery.

The quantity of reducing agent used must be sufficient to generate a catalytically effective copper-activated silicon for the stable, selective and rapid Direct Synthesis of trialkoxysilanes. At a minimum, it must be that quantity which is stoichiometrically required to fully reduce the divalent or monovalent copper to zerovalent copper. Oxidized copper may be present in the bulk catalyst as, for example, in copper (II) hydroxide and copper (I) oxide, or at surfaces as, for example, in copper powders. In practice, many times that amount is used on account of the decreased probability of contact brought about by the greater mass, number and surface area of the silicon particles present in the mixture.

Standard commercial grade hydrogen gas, carbon monoxide or monosilane is suitable for the activation step of the instant invention. Additionally, the hydrogen gas produced as a byproduct of the Direct Reaction of alcohols with silicon is also suitable. As has already been recited hereinabove, this hydrogen gas may contain nitrogen, argon, hydrocarbons and ethers. While it is desirable to remove these other gases, for example by adsorption, prior to recycle of the hydrogen to the activation step, this purification step is not absolutely essential.

Polyaromatic hydrocarbons, for example those described hereinabove as solvents and heat transfer fluids, have been found to be suitable reducing agents for the catalyst precursors of this invention. Reduction of the catalyst precursor, or its mixture with silicon, is carried out in a slurry reactor at temperatures below the boiling point of the polyaromatic hydrocarbon, which is then separated from the solids prior to the Direct Synthesis in alkylated benzene solvents. Following separation, the recovered polyaromatic hydrocarbon can be used again in subsequent reductive activations.

Activation of silicon-copper catalyst precursor mixtures with carbon monoxide (CO) or monosilane ($SiH_4$) is conducted in the same manner as described above for hydrogen. Appropriate safety precautions must be followed in handling $SiH_4$ on account of its pyrophoricity.

REACTION CONDITIONS

Designs, descriptions and operational considerations pertinent to three phase reactors are contained in the following monograph, articles and patents:

P. A. Ramachandran and R. V. Chaudhari, Three Phase Catalytic Reactors, Gordon and Breach Science Publishers, New York, 1983

A. N. Gartsman, et al., International Chemical Engineering, vol. 17 (1977) pp 697–702

D. H. Ying, et al., Industrial & Engineering Chemistry, Process Design & Development, vol. 19 (1980) pp 635–638

C. N. Satterfield, et al., Chemical Engineering Science, vol. 35 (1980) pp 195–202

J. M. Boxall, et al., Journal of Metals, (August 1984) pp 58–61

W. Roeckel, C. Scaccia and J. Conti, U.S. Pat. No. 4,328,175 (May 4, 1982)

L. M. Litz, U.S. Pat. No. 4,454,077 (Jun. 12, 1984)

Reactors which are used in carrying out the process of the present invention may be operated in a batchwise or continuous mode. In batchwise operation, a single addition of silicon and copper catalyst is made to the reactor at the outset and alcohol is added continuously, or intermittently, until the silicon is fully reacted, or reacted to a desired degree of conversion. In continuous operation, silicon and copper catalyst are added to the reactor initially and thereafter to maintain the solids content of the slurry within desired limits. The batchwise mode is illustrated in U.S. Pat. No. 4,727,173 and the continuous mode in U.S. Pat. No. 5,084,590. Both of these patents are incorporated herein by reference.

In its preferred form in accordance with the present invention, the Direct Synthesis of trialkoxysilanes is conducted in a continuously agitated slurry reactor with a hydrogen activated silicon-copper catalyst mixture. The reactor may have a single nozzle or multiple nozzles for the introduction of gaseous alcohol. A means of continuous or intermittent addition of activated silicon-copper catalyst mixture, or of silicon, is also provided. Means for continuous removal and recovery of the volatile reaction products and unreacted alcohol are also desirably provided. Separation and purification of the trialkoxysilane products are optimally performed in the manner disclosed in U.S. Pat. No. 4,761,492 or U.S. Pat. No. 4,999,446, both of which are incorporated herein by reference. Hydrogen gas in the gaseous reaction product is optionally recovered for use in the activation step.

When the initial loading of silicon and copper catalyst precursor is activated with hydrogen according to the method of the instant invention, continuous slurry phase Direct Synthesis of trialkoxysilanes is advantageously continued by adding only silicon, or silicon containing less copper catalyst than that initially added. In this way, the copper concentration of the slurry is controlled to minimize the transformation of the alcohol to hydrocarbons and water (Equations 3 and 5 above). Disadvantages caused by water have been recited hereinabove.

The reaction is generally conducted at temperatures above about 150° C., but below such a temperature as would degrade or decompose the reactants or solvents. Preferably, the reaction temperature is maintained in a range from about 200° C. to about 260° C. The reaction of methanol with the copper-activated silicon of the present invention is preferably operated at 220°–250° C., whereas the reaction of ethanol is preferably operated at 200°–240° C. The pressure at which the reaction is conducted is not critical and can be varied from subatmospheric to superatmospheric. Atmospheric pressure is generally employed.

Preferably, the contents of the reaction mixture are agitated to maintain a well mixed slurry of the copper-activated silicon particles and gaseous alcohol in the solvent. The reaction mixture is preferably well insulated to assure that the trialkoxysilane does not reflux in the reactor. Refluxing can encourage the consecutive reaction of the trialkoxysilane with the alcohol, resulting in loss of the desired trialkoxysilane product by the formation of the tetraalkoxysilane.

The presence of gaseous alcohol, hydrogen gas and other gases in the reactor can occasionally lead to foaming. This is undesirable since it can result in loss of solvent and copper-activated silicon from the reactor. It has been found that the addition of foam control agents, preferably silicon-containing foam control agents such as OSi Specialties SAG® 1000, SAG® 100, SAG® 47 and Dow Corning FS-1265, will negate or ameliorate this problem. SAG® 1000, SAG® 100 and SAG® 47 are compositions comprising polydimethylsilicones and silica. FS 1265 contains fluorinated silicones, for example, poly(dimethylsiloxane-co-trifluoropropylmethylsiloxane). The foam control agent must be durable such that a single addition at the outset of a batch reaction is sufficient to avoid or mitigate foam formation until all of the silicon has been consumed.

At constant temperature, the reaction rate depends on the surface area and particle size of the silicon and on the feed rate of the alcohol. Higher rates are obtained at higher surface areas, finer particle sizes and higher feed rates. These parameters are selected so that a safe, economically sustainable product output is realized without endangerment to people, property and the environment. For example, silicon of 25–75μ can be used to minimize side reactions and obtain high rates and selectivity to $HSi(OC_2H_5)_3$ at about 230° C., in place of 100–400μ silicon at about 250° C.

High selectivity to trialkoxysilanes, high reaction rates and stable performance are realized when the activated silicon-copper product of the present invention is utilized. This is particularly so when alkylated benzenes are the solvents. With these solvents and the conventional thermally activated silicon-copper mixture, used for example in U.S. Pat. No. 4,727,173, selectivity to trialkoxysilanes decreases after 25–30 weight percent silicon conversion and formation of alkyl silicates, methane and silicate gels increases. These trends are reversed after about 50–60 weight percent silicon conversion. Such instability is undesirable and not conducive to the successful operation of a commercial scale Direct Synthesis. Use of the hydrogen, carbon monoxide, monosilane or other reductive activation method of the instant invention prevents this catalytic instability and affords high, stable selectivities and rates throughout the duration of a reaction.

PERFORMANCE ADVANTAGES

In accordance with the present invention, the following substantial advantages are realized in the Direct Synthesis of trialkoxysilanes when using silicon-copper catalyst slurries prepared by reductive activation as described herein.

Improved yield of trialkoxysilanes in alkylated benzenes and polyaromatic hydrocarbon solvents Stable reaction in alkylated benzenes No loss of selectivity to trialkoxysilane at <50% silicon conversion.

Significantly lower hydrocarbon (e.g. methane), water and silicate byproduct formation.

Faster reaction rates.

More efficient use of raw materials: silicon, alcohol and catalyst

EXAMPLES

The following Examples illustrate the preferred embodiments of the instant invention. These are not intended to limit the scope of the invention. Rather, they are presented merely to facilitate the practice of the invention by those of ordinary skill in the art.

ABBREVIATIONS AND UNITS USED

Abbreviations used in the presentation of the data of the illustrative examples are the following:

| ABBREVI-ATION | MEANING | ABBREVI-ATION | MEANING |
|---|---|---|---|
| TMS | $HSi(OCH_3)_3$ | g | gram |
| TTMS | $Si(OCH_3)_4$ | kg | kilogram |
| TES | $HSi(OC_2H_5)_3$ | L | liters |
| SEL | $HSi(OR)_3$/ $Si(OR)_4$ | μ | micron |
| % Si/hr | percent silicon converted per hour | $m^2/g$ | square meters per gram |
| N600L | Nalkylene ® 600L | rpm | revolutions per minute |
| N550BL | Nalkylene ® 550BL | wt % | weight percent |
| TH59 | Therminol ® 59 | min | minute |

DESCRIPTION OF FIG. 1

A schematic drawing of this reactor and its ancillary equipment is shown in FIG. 1. Alcohol is delivered from the reservoir (1) via the pump (2), flow meter (3) and vaporizer (4) to the reactor (5). Separate coils for methanol and the recycle stream are contained within the vaporizer. The reactor contains silicon and copper catalyst suspended and dispersed in a high boiling solvent. A foam control agent is optionally present. Provision is made for nitrogen injection upstream of the vaporizer and hydrogen injection downstream of the vaporizer as shown in the Figure. Alcohol reacts with the copper-activated silicon in the reactor. The reactor is fitted with a hopper (6) for solids, an agitator (7), heater and temperature controller (8), thermocouple bundle (9), internal baffles (10), spargers (11), pressure gauge (12) and pressure release safety valve (13). The gaseous reaction mixture leaves the reactor via the entrainment separator (14). Valve (15) permits sampling of the reaction mixture and venting of water vapor during the hydrogen activation step. (16) is an assembly of distillation columns adequate for the separation of unreacted alcohol and lower boilers from the desired trialkoxysilane. The columns are connected to a reboiler (17) and reflux condenser (18). Liquid reaction product (19) containing the desired trialkoxysilane and byproducts with higher boiling points is discharged from the unit to storage containers via the pump (20). The temperatures of the columns and reboiler are controlled such that stream (21) contains the byproduct gases, unreacted alcohol, alkoxysilanes and azeotropes boiling lower than the desired trialkoxysilane. A portion (22) of the liquid overhead stream is returned to the distillation columns as reflux flow. The remainder (23) is recycled through the vaporizer and reinjected into the reactor so that its contained alcohol can be reacted with copper-activated silicon. The vent gas stream (24) is admitted into a flowmeter capable of measuring total gas flow.

EQUIPMENT USED FOR ILLUSTRATIVE EXAMPLES

A 5.8 liter Chemineer® reactor was used for all of the illustrative Examples presented here. Four 90° spaced, 1.27 cm wide baffles were affixed to the wall of the reactor. Agitation was provided by two stirrers attached to an axial shaft. The bottom one was a six blade turbine, 6.35 cm in diameter. A four blade propeller of the same diameter was placed 10 cm above the turbine. Power for agitation was provided by a variable speed air-driven motor whose rotational speed was measured by a magnetic tachometer. An electric heating mantle controlled by a heater/temperature controller was used to heat the reactor.

Methanol or ethanol was supplied to the reactor from a 1 L storage container via a calibrated FMI laboratory pump. Coiled stainless steel tubing, 0.32 cm internal diameter×305 cm length, placed in a 4 L silicone oil bath controlled at 150° C. served as the alcohol vaporizer. A similar vaporizer coil was available for the recycle stream, but it was not used during the course of these experiments. The alcohol inlet line entered through the top of the reactor. It was heat traced to prevent condensation of the vapor. Alcohol vapor was injected 2.5 cm from the bottom of the reactor and below the level of the six-blade turbine through a single downward pointing (0.63 cm internal diameter) sparger. A pressure gauge attached the alcohol vapor inlet line gave higher readings (up to about 2 atmospheres) when the sparger was plugged. Ordinarily, the gauge was at zero. Additional alcohol was supplied to the storage container during an experiment to maintain an uninterrupted flow of this reagent.

Reaction products and unreacted alcohol exited the reactor through a 91.4 cm×2.54 cm internal diameter packed tube, which served as entrainment separator and partial distillation column to remove solvent and higher boiling silicates from the product stream. The packing material was ceramic saddles and stainless steel mesh. Five thermocouples were distributed along the length of the tube to record temperatures and indicate foaming. The lowest thermocouple was flush with the top of the reactor. As was indicated hereinabove, foaming was controlled by the use of FS 1265 and SAG® antifoaming compounds. Flexible tubing connected the outlet of the entrainment separator/partial distillation column to the four-way valve (15 in FIG. 1).

Two ten plate Oldershaw distillation columns served to separate the liquid reaction products and unreacted alcohol from the gases. Effluent from the reactor was admitted into the lower column, which was attached to a 3 neck 2 L round bottom flask supported in a heating mantle. The upper column was capped by a magnetically controlled reflux condenser and distillation head with thermocouple. The reflux condenser and another condenser downstream were cooled to −25° C. by circulating silicone oil. Uncondensed gases exited the condenser through a vapor lock gas bubbler into the total gas flow meter (Model DTM-115, American Meter Co.). Wider tubing was employed downstream of the bubbler to avoid backpressures likely to shatter the glassware (columns, condensers and bubbler) or cause leaks at the joints. The bubbler contained silicone oil and had an extra opening for release of overpressure. A gas sampling port was provided at a T joint following the gas meter. Gas flow from the meter was diluted with nitrogen prior to its discharge into the laboratory hood. A thermocouple was located in the second opening of the three neck flask and the intake to an FMI laboratory pump in the other. The pump was used to transfer liquid product from the flask to Teflon coated Nalgene® storage bottles. All glass containers for sampling and storage of the crude trialkoxysilane product were acid washed, alcohol rinsed and oven dried prior to use.

GENERAL ACTIVATION AND REACTION PROCEDURE

Typically, the reactor was charged with 2 kg solvent, 1 kg silicon, copper catalyst precursor (copper(II) hydroxide) and 0.6 g FS-1265 defoamer and sealed. According to equation (1), complete conversion of 1 kg silicon will require 3.43 kg methanol (4.93 kg ethanol) and produce 4.36 kg HSi(OCH$_3$)$_3$ (5.86 kg HSi(OC$_2$H$_5$)$_3$) and 873 L H$_2$ at 298K and 1 atmosphere. The slurry was agitated at ~900 rpm and nitrogen introduced as it was heated to 250° C. Unless otherwise stated, hydrogen gas was injected at 150° C. through the alcohol sparger and its flow maintained for 30 minutes after the final temperature (250° C.) had been reached. The total H$_2$ flow was recorded. During the hydrogen activation, gas flow from the reactor was vented through the four-way valve and not admitted to the distillation contains until the hydrogen flow was terminated. Simultaneous with the hydrogen activation, the alcohol vaporizer was heated to ~150° C. and the refrigerant circulated through the reflux condenser was cooled to −25° C. Alcohol flow to the reactor was initiated when gas chromatographic analysis of the effluent stream (24 in FIG. 1) showed that there was no residual hydrogen left from the activation step. Comparative experiments (see Example 1) were run with nitrogen as the only injected gas during the catalyst activation step.

Once the alcohol flow was underway, sampling and analysis of the vent gas stream (24 in FIG. 1) for hydrogen were done every 10–15 minutes until a stable composition was established. That indicated the end of the induction period. Thereafter, gas sampling was done every 30 minutes to monitor hydrogen, hydrocarbons and ethers. During the course of the reaction, total vent gas flow was used as an approximate measure of the reaction rate according to the stoichiometry of equation (1).

Samples were collected in acid washed, alcohol rinsed, dried refrigerated containers attached at the four-way sampling valve (15 in FIG. 1) for 2–5 minutes every half hour. They were weighed and analyzed by gas chromatography. The bulk of the liquid product was condensed in the three neck flask which served as the reboiler (17 in FIG. 1 ) and transferred to storage. All of these data were used to calculate the temporal composition of the product stream, its selectivity to trialkoxysilane, the reaction rate and overall silicon conversion. Usually, reactions were terminated after >85% of the silicon charged to the reactor had been reacted. In some cases, terminations were made at lower and higher silicon conversions depending on the objective of the experiment.

Gas samples were analyzed for hydrogen, nitrogen and hydrocarbon (e.g. methane, ethane) content on a Hewlett Packard 5840 gas chromatograph fitted with a GS-Molesieve 30 m×0.53 mm internal diameter (J & W Scientific) capillary column and flame ionization detector. Argon was the carrier gas. Gas chromatography-mass spectrometry was used to analyze for dimethyl and diethyl ether. Liquid samples containing alkoxysilanes were analyzed on a Hewlett Packard 5890 gas chromatograph with a 3.66 m×3.18 mm internal diameter stainless steel column packed with 20% OV-101 on 60/80 mesh Chromosorb WHP.

Used solvent was analyzed by gravimetry and atomic absorption spectroscopy for total silicon content and by $^{29}$Si NMR for the specification of the soluble silicon into $Q^0$, $Q^1$, $Q^2$ and $Q^3$ groups. The chemical shifts (relative to tetramethylsilane) of these functional groups are set forth below. Molar percentages of these groups are calculated from the integration areas.

| GROUP | STRUCTURE | $^{29}$Si NMR SHIFTS (ppm) |
|---|---|---|
| $Q^0$ | Si(OR)$_4$ | −78.3 to −78.5 |
| $Q^1$ | O—Si(OR)$_3$ | −85.6 to −85.9 |
| $Q^2$ | O—Si(OR)$_2$—O | −93.6 to −93.9 |
| $Q^3$ | O—Si—O(OR)O | −102.0 to −102.6 |

MATERIALS USED

Technical grade silicon samples utilized in the experiments of the illustrative Examples are listed in Table 1 along with relevant analytical data. Table 2 presents a data summary for the copper catalysts used. NALKYLENE® 550BL, NALKYLENE® 600L, THERMINOL® 59 and MARLOTHERM® S were the solvents used. FS 1265 was the foam control agent.

TABLE 1

COMPOSITION OF SILICON SAMPLES USED IN ILLUSTRATIVE EXAMPLES

| ELEMENT | SAMPLE Si-1 | SAMPLE Si-2 |
|---|---|---|
| Al, wt % | 0.2 | 0.08 |
| Ba, ppm | 13.4 | <3 |
| Ca, ppm | 517 | 600 |
| Cr, ppm | 28.6 | 58.9 |
| Cu, ppm | 19.5 | 34.8 |
| Fe, wt % | 0.39 | 0.38 |
| Mg, ppm | 23.9 | 8.8 |
| Mn, ppm | 125 | 90.4 |
| Ni, ppm | <10 | 15.5 |
| P, ppm | 25 | 26.8 |
| Pb, ppm | <10 | <10 |
| Sn, ppm | <10 | <10 |
| Ti, ppm | 312 | 299 |
| V, ppm | 20.5 | 14.3 |
| Zn, ppm | 6.6 | <5 |
| Zr, ppm | 100 | 29 |
| Si | balance | balance |

PARTICLE SIZE DISTRIBUTION OF SILICON SAMPLES USED IN ILLUSTRATIVE EXAMPLES

| NOMINAL SIEVE SIZE, μ | Wt % > NOMINAL SIZE, Si-1 | Wt % > NOMINAL SIZE, Si-2 |
|---|---|---|
| 600 | 0 | 3.1 |
| 425 | 0 | 14.0 |
| 300 | 1.6 | 18.7 |
| 250 | 28.4 | 13.7 |
| 180 | 30.3 | 11.9 |
| 75 | 39.5 | 24.1 |
| <75 | 0.1 | |
| 45 | | 1.5 |
| <45 | | 11.6 |

TABLE 2

CHARACTERIZATION OF COPPER (II) HYDROXIDE USED IN ILLUSTRATIVE EXAMPLES

| PROPERTY | VALUE |
|---|---|
| Cu, wt % | 57.50 |
| Al, ppm | 340 |
| As, ppm | <30 |
| Ca, wt % | 0.11 |
| Fe, ppm | 670 |
| P, wt % | 1.58 |
| Pb, ppm | 250 |
| Sb, ppm | 70 |
| Sn, ppm | <50 |
| Zn, wt % | 0.17 |
| H$_2$O, wt % | 6.0 |
| Cl, ppm | 310 |
| SO$_4^{2-}$, wt % | 2.89 |
| Surface Area, m$^2$/g | 37 |
| Particle Size Range, μ | 0.1–20 |
| Average Particle Size, μ | 1.37 |

Examples 1A–1C (Comparative Examples)

This Example illustrates the Direct Synthesis of trimethoxysilane in alkylated benzene (NALKYLENE® 550BL and NALKYLENE® 600L) and diphenyl ethane (THERMINOL® 59) solvents using the conventional, thermally activated silicon-copper mixture prepared in the presence of nitrogen. It is a comparative Example and is not of this invention.

Figure 2:
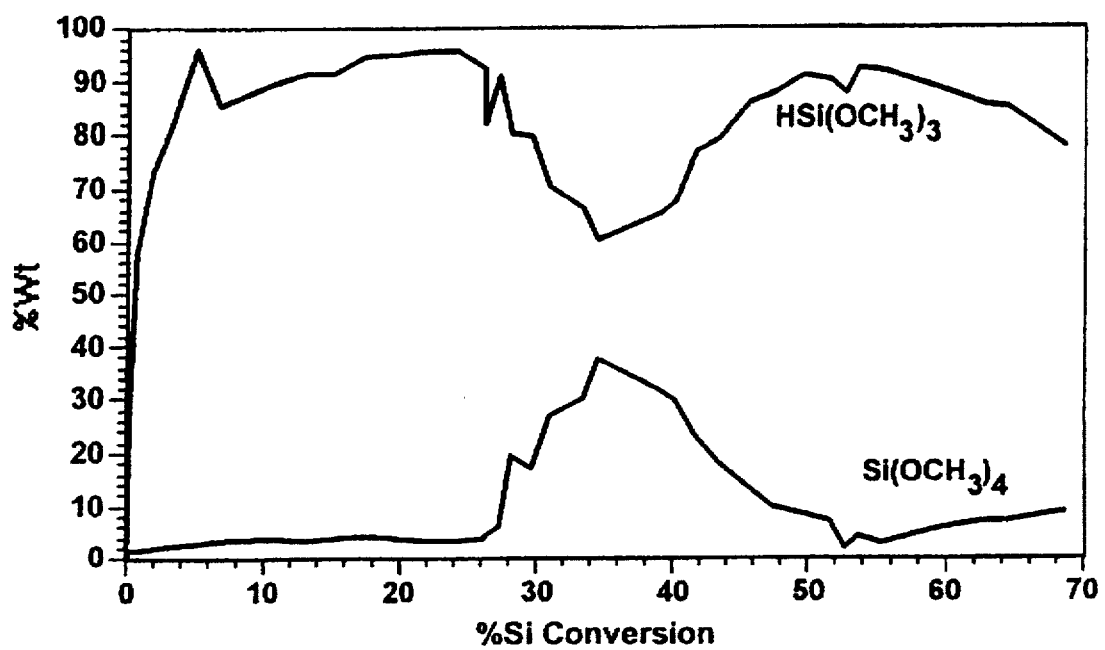
FIG. 2 represents the variation of $HSi(OCH_3)_3$ and $Si(OCH_3)_4$ formation with silicon conversion in Nalkylene® 600L. (Example 1A).
Figure 3:
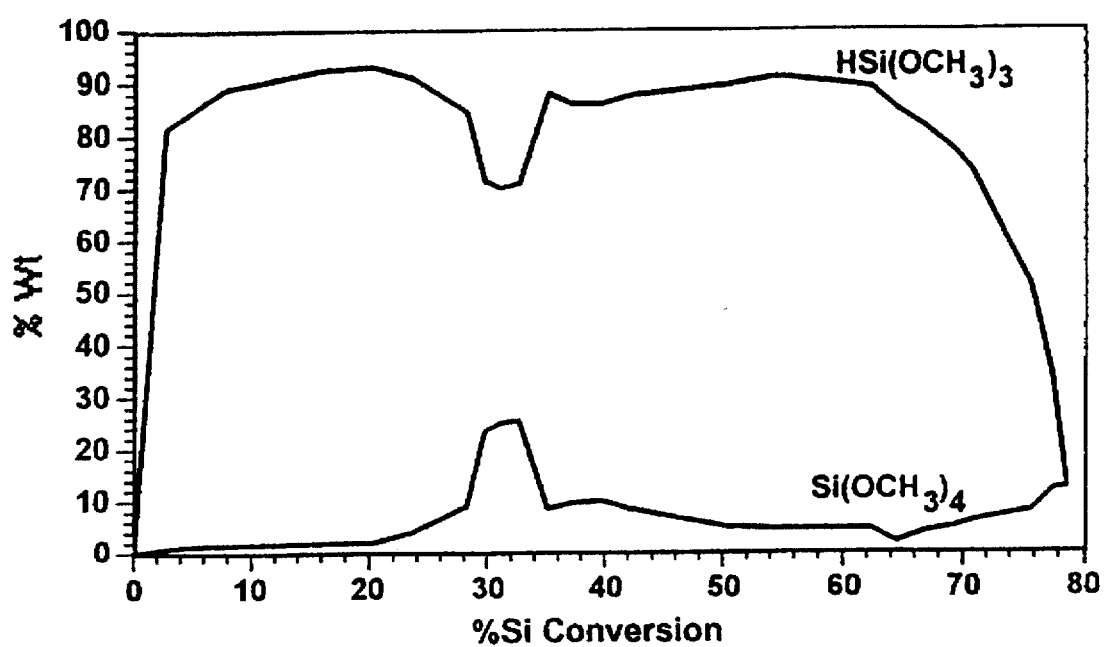
FIG. 3 represents the variation of $HSi(OCH_3)_3$ and $Si(OCH_3)_4$ formation with silicon conversion in Nalkylene® 550L. (Example 1B).
Figure 4:
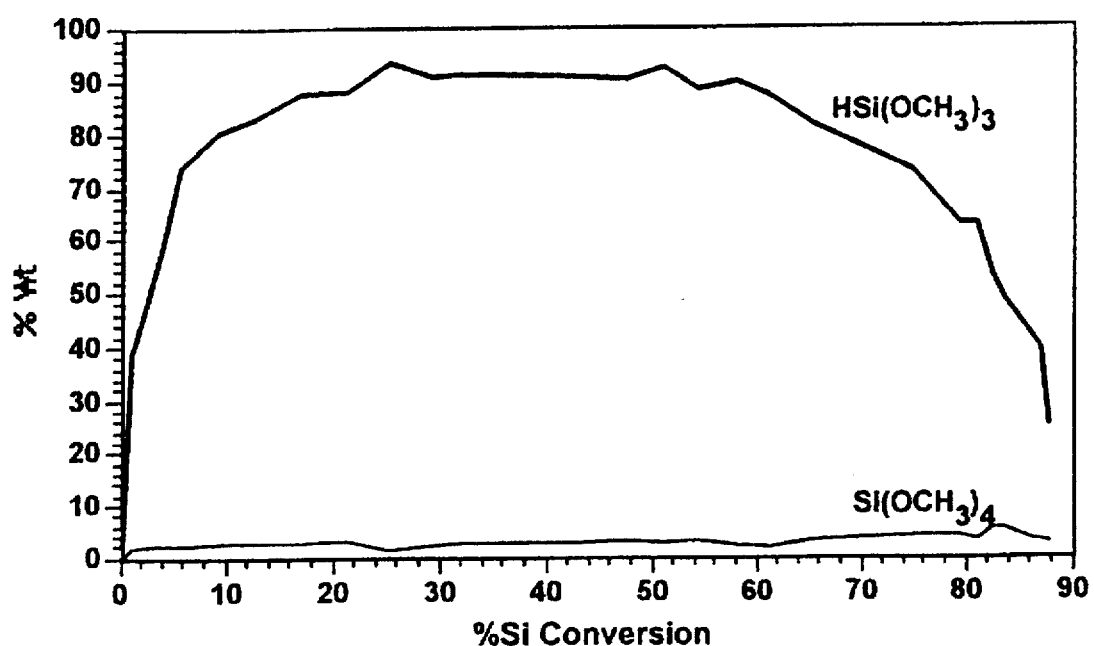
FIG. 4 represents the variation of $HSi(OCH_3)_3$ and $Si(OCH_3)_4$ formation with silicon conversion in Therminol® 59. (Example 1C).
Figure 5:
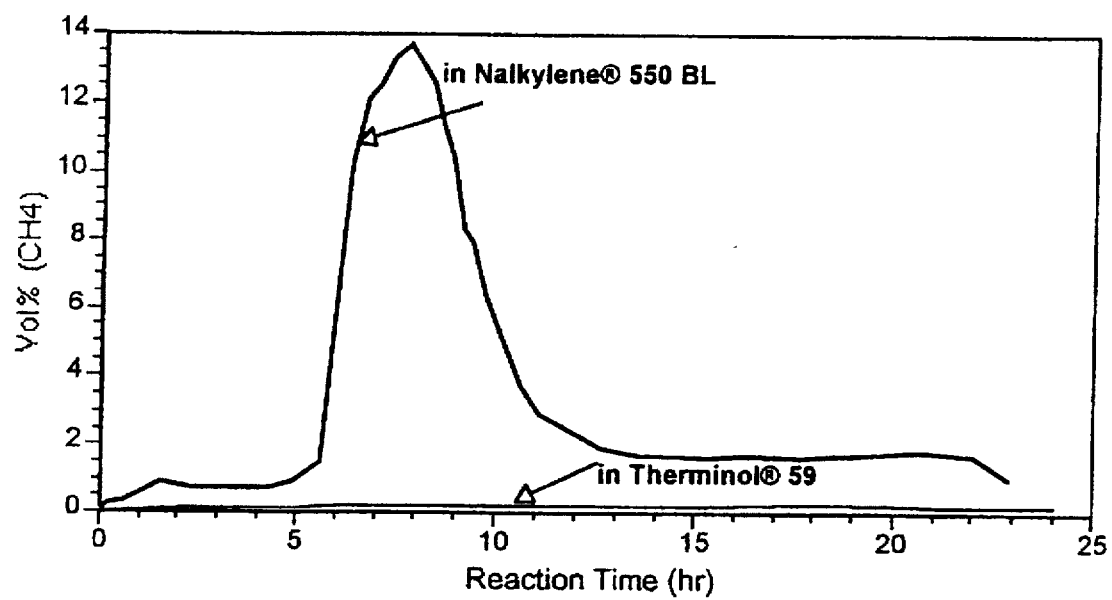
FIG. 5 represents $CH_4$ formation during $HSi(OCH_3)_3$ direct synthesis in Nalkylene® 550BL and Therminol® 59.

Each of the Examples 1A–1C was performed at 250° C. with a methanol feed rate of 3.3 g/min in the apparatus of FIG. 1 using the procedure described above. Silicon sample Si-1 (1 kg), copper (II) hydroxide catalyst (7.05 g), FS 1265 (0.6 g) and 2 kg solvent were the quantities used in all experiments. Table 3 presents a summary of the experimental data collected for each experiment. FIGS. 2–4 show the variation of HSi(OCH$_3$)$_3$ and Si(OCH$_3$)$_4$ with silicon conversion. FIG. 5 shows methane composition of the effluent gas over the course of the experiments of Examples 1B and 1C.

The reaction residues from the three experiments were different in appearance. That from Examples 1A and 1B was a black, sticky gel containing silicon particles. On its settling, a black fluffy solid formed atop the agglomerated silicon particles. Reaction residue from Example 1C was reddish brown. After it settled, a fluffy reddish brown solid was observed above unagglomerated silicon particles. These observations suggest that water formation in the reaction mixtures containing the alkylated benzene solvents led to gel formation. This gel caused agglomeration of the silicon particles in the residues of Examples 1A and 1B.

TABLE 3

COMPARISON OF HSi(OCH$_3$)$_3$ DIRECT SYNTHESIS IN NALKYLENE ® 600L, NALKYLENE ® 550BL AND THERMINOL ® 59

| Example | Solvent | React. Time, hr | Si Conv. % | Rate, % Si/hr | TMS, kg | TTMS, kg | SEL |
|---|---|---|---|---|---|---|---|
| 1A | N600L | 22.2 | 79 | 3.56 | 2.85 | 0.37 | 7.65 |
| 1B | N550BL | 23.73 | 78.5 | 3.31 | 3.01 | 0.27 | 11.14 |
| 1C | TH59 | 22.7 | 85 | 3.75 | 3.54 | 0.13 | 27.10 |

It is clear from the data that the Direct Synthesis of HSi(OCH$_3$)$_3$ proceeded with higher rate and selectivity in THERMINOL® 59 than in the alkylated benzene solvents, NALKYLENE® 600L and NALKYLENE® 550BL.

Moreover, as FIGS. 2–4 illustrate, the reaction in THERMINOL® 59 afforded >80 wt % HSi(OCH$_3$)$_3$ between 10–70% silicon conversion while those in the NALKYLENE® solvents showed a temporary loss of selectivity to <80 wt % HSi(OCH$_3$)$_3$ between 20–50% silicon conversion. FIG. 5 shows that a sharp increase in methane formation coincided with the period of decreased selectivity in the experiment of Example 1B. Dimethyl ether formation was also increased during this period. These increases in methanol decomposition products were not observed for the reaction performed in THERMINOL® 59 (Example 1C).

TABLE 4

SILICON AND SILICATE COMPOSITION OF USED REACTION SOLVENTS

| EXAMPLE | wt % Si in SOLVENT | Q$^0$, mole % | Q$^1$, mole % | Q$^2$, mole % | Q$^3$, mole % |
|---------|--------------------|---------|---------|---------|---------|
| 1A | 0.91 ± 0.04 | 1.79 | 47.39 | 37.03 | 11.36 |
| 1B | 0.87 ± 0.06 | 0 | 44.2 | 39.8 | 13.8 |
| 1C | 0.34 ± 0.02 | 0 | 52.3 | 47.7 | 0 |

Solvent from each of the reactions of Example 1 was centrifuged at 1500 rpm for 5 minutes to remove suspended silicon and copper particles. The supernate was analyzed for total soluble silicon by gravimetry and for silicon speciation by $^{29}$Si nmr. The analytical results set forth in Table 4 show that, even though the reaction in THERMINOL® 59 (Example 1C) was continued to a higher silicon conversion than those in the NALKYLENE® solvents (Examples 1A, 1B), the residual silicon content of the used THERMINOL® 59 was lower than that of used NALKYLENE® solvents. Additionally, there appeared to be relatively more branching groups (Q$^3$) in the soluble silicates contained in the NALKYLENE® solvents (Examples 1A and 1C) and more terminal groups (Q$^1$) in THERMINOL® 59 (Example 1C).

Example 2

This Example illustrates the use of hydrogen to activate silicon-copper catalyst mixtures for reactions run in alkylated benzene solvents.

The experiment was done with NALKYLENE® 600L, silicon sample, Si-1, and copper (II) hydroxide using the same quantities already reported for Example 1A. Hydrogen gas was introduced into the reaction slurry between 20°–250° C. Total hydrogen activation time was 90 minutes and the total hydrogen flow was 188.5 liters.

Methanol was introduced at 3.3 g/min when there was no longer any hydrogen from the activation step in the reactor exhaust. Reaction was continued until approximately 70 weight percent of the silicon had been reacted. After settling, the reaction residue showed a fluffy reddish brown layer atop free flowing silicon particles similar to the two layers observed in the experiment of Example 1C. A small amount of methane formation was observed during the first two hours of reaction (up to ~8% Si conversion), but none thereafter. Both of these results are consistent with reduced water and gel formation consequent to the use of hydrogen activation.

HSi(OCH$_3$)$_3$ was >80 wt % between 10–70% silicon conversion. Table 5 compares the quantities of the principal products formed with those at the corresponding point (67% Si Conversion) of Example 1A. It is clear from these data and the observations of this experiment that hydrogen activation exerted a beneficial effect on the selectivity and stability of HSi(OCH$_3$)$_3$ formation.

TABLE 5

EFFECT OF HYDROGEN ACTIVATION ON HSi(OCH$_3$)$_3$ DIRECT SYNTHESIS IN NALKYLENE ® 600 L AT 250° C.

| EXAMPLE | Si CONV.,% | RATE % Si/hr | TMS, kg | TTMS, kg | SEL. |
|---------|-----------|--------------|---------|----------|------|
| 1A | 67.0 | 3.68 | 2.10 | 0.29 | 7.24 |
| 2 | 66.9 | 3.66 | 2.57 | 0.27 | 9.52 |

Residual silicon content of the used NALKYLENE® 600L of this Example was 0.31±0.05 wt %. It was approximately three times less than that of Example 1A. This is a desirable result since it indicates that the hydrolysis and condensation reactions associated with the presence of water occurred to a significantly reduced extent when hydrogen activation was employed. Also in agreement with this conclusion were the $^{29}$Si nmr data: Q$^0$=2.84 mole %, Q$^1$=56.16 mole %, Q$^2$=30.57 mole % and Q$^3$=6.69 mole which indicated more end groups (Q$^1$) and fewer chains or cycles (Q$^2$) and branches (Q$^3$) than were present in the used solvent of Example 1A (see Table 4).

Example 3

The experiments of this Example illustrate hydrogen activation of silicon-copper (II) hydroxide mixtures in NALKYLENE® 550BL at 150°–250° C. Hydrogen use was varied from 190.7 liters to 1190.5 liters in the three experiments of this Example.

Figure 6:
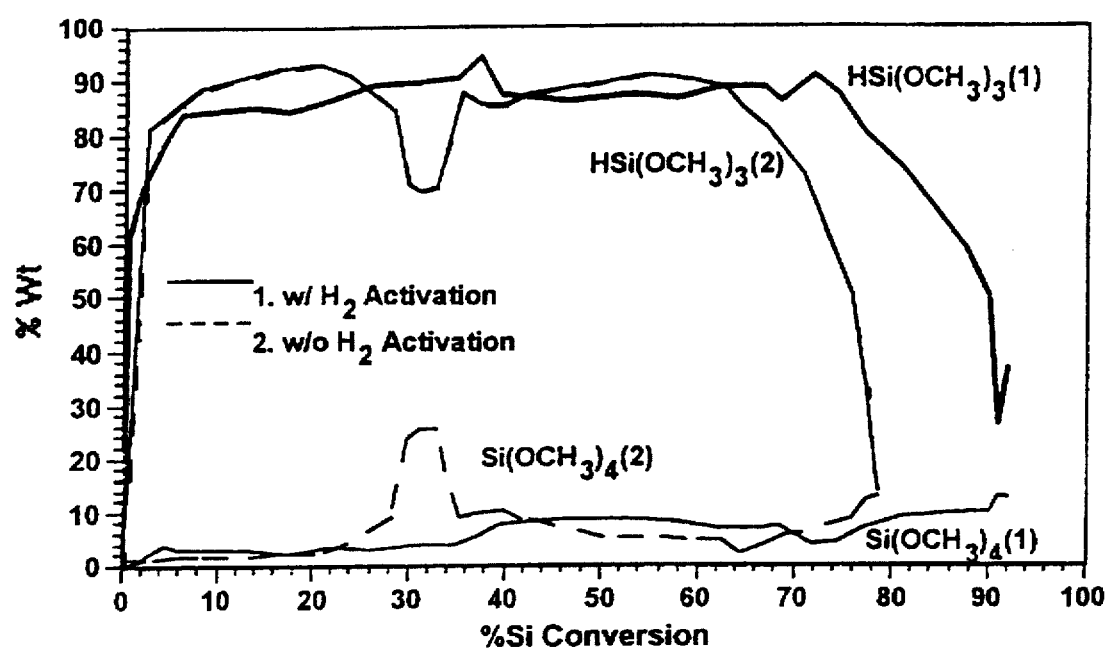
FIG. 6 represents the effect of $H_2$ activation of silicon-copper catalyst slurry on $HSi(OCH_3)_3$ and $Si(OCH_3)_4$ formation in Nalkylene® 550BL.

All three experiments of this Example were done as described in the general procedure above. NALKYLENE® 550BL was the solvent used in each experiment. Hydrogen gas was introduced at 150° C. and its flow was maintained for 30 minutes after the reaction mixture had reached 250° C. The volumes of hydrogen used in each experiment are shown in Table 6. On a molar basis, the hydrogen used far exceeded the 0.064 moles (1.56 L) required to reduce the Cu(II) contained in 7.05 g copper (II) hydroxide charged in each experiment. This excess was necessary because of the larger mass and surface area of silicon particles relative to Cu(OH)$_2$ present in the slurry. FIG. 6 and Table 6 present summaries of the experimental data.

FIG. 6 shows plots of HSi(OCH$_3$)$_3$ and Si(OCH)$_4$ formation over the course of the experiments of Examples 3A, 3B, and 3C. It is immediately apparent that these reactions did not exhibit the instability observed at 28–36% silicon conversion in the experiment of Example 1B. It is also observed that an increase in the volume of hydrogen lengthened the duration of the period of elevated (>80 wt %) HSi(OCH$_3$)$_3$ selectivity.

TABLE 6

IMPROVEMENT IN HSi(OCH$_3$)$_3$ DIRECT SYNTHESIS WITH INCREASING HYDROGEN USE DURING ACTIVATION STEP

| EXAMPLE | Si CONV.,% | RATE % Si/hr | TMS, kg | TTMS, kg | SEL. |
|---------|-----------|--------------|---------|----------|------|
| 1B: CONTROL | 78.5 | 3.31 | 3.01 | 0.27 | 11.14 |
|  | 70.0 | 3.62 | 2.72 | 0.19 | 14.31 |
| 3A: 190.7 L H$_2$ | 83.89 | 3.85 | 3.30 | 0.24 | 13.75 |
|  | 70.0 | 4.00 | 2.80 | 0.17 | 16.47 |
| 3B: 451.3 L H$_2$ | 92.97 | 4.00 | 3.78 | 0.31 | 12.19 |
|  | 70.0 | 4.35 | 2.89 | 0.17 | 17.00 |
| 3C: 1190.5 L H$_2$ | 89.82 | 3.87 | 3.66 | 0.29 | 12.62 |
|  | 71.0 | 4.28 | 2.96 | 0.17 | 17.41 |

For example, whereas Example 1B showed a precipitous decline in HSi(OCH$_3$)$_3$ selectivity after about 70% silicon conversion and Example 3A showed a similar decline after about 76% silicon conversion, that decline occurred after >80% silicon conversion for Examples 3B and 3C. Higher selectivities to HSi(OCH$_3$)$_3$ at higher silicon conversions result in higher yields of this desirable product. These higher yields of HSi(OCH$_3$)$_3$ and correspondingly lower yields of Si(OCH$_3$)$_4$ are reflected in the data of Table 6. HSi(OCH$_3$)$_3$ yield increased by 20–26% with the use of 190–1200 liters H$_2$ during activation. The accompanying rate increase was approximately 30%. However, since each of the experiments was stopped at a different point, Table 6 also includes performance comparisions for ~70% silicon conversion to illustrate the performance improvements.

Figure 7:
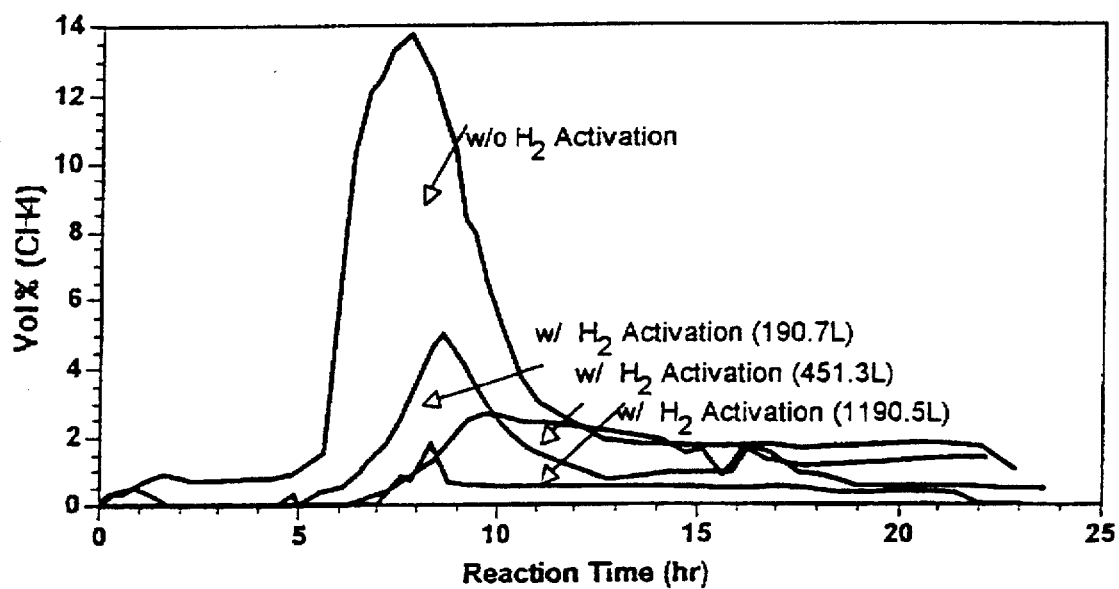
FIG. 7 represents the effect of $H_2$ activation of silicon-copper catalyst slurry on $CH_4$ formation during $HSi(OCH_3)_3$ direct synthesis.

FIG. 7 shows methane formation profiles for Examples 1B, 3A, 3B and 3C. It is clear that methane formation declined with increasing hydrogen usage during the activation step. In fact, methane formation in Example 3C was ~17 times less than in Example 1B. Table 7 shows that the decreased methane formation correlated with the lower soluble silicon levels remaining in the post-reaction solvent. Soluble silicon was 2–3 times lower when hydrogen activation was employed. The absence of branching groups (Q$^3$) and the predominance of terminal groups (Q$^1$) confirm that these lower soluble silicon levels were the result of lower water and lower condensed gel formation.

TABLE 7

CORRELATION OF METHANE FORMATION IN EXAMPLES 3A, 3B AND 3C AND THE SILICON AND SILICATE CONTENT OF THE USED SOLVENT

| Ex- ample | wt % Si in Solvent | CH$_4$ Ratio | Q$^0$ mole % | Q$^1$ mole % | Q$^2$ mole % | Q$^3$ mole % |
|---|---|---|---|---|---|---|
| 3A | 0.84 | 5.03 | 4.1 | 55.6 | 40.2 | 0.0 |
| 3B | 0.50 | 2.78 | 3.3 | 62.8 | 33.9 | 0.0 |
| 3C | 0.43 | 1.00 | 4.7 | 64.0 | 31.3 | 0.0 |

Example 4

This Example illustrates the improvements in reaction rate and selectivity to HSi(OCH$_3$)$_3$ when hydrogen activation is used for Direct Syntheses conducted in polyaromatic hydrocarbon solvents such as THERMINOL® 59.

The experiment of this example was performed in THERMINOL® 59 using the general procedure described above. The volume of hydrogen gas used in the activation was 1803.9 liters. Reaction was terminated after 24.9 hours. Results are summarized in Table 8 along with those of the comparative Example 1C.

Since the reactions were sustainable to different levels of silicon conversion, data are also shown at 85% silicon conversion to facilitate comparison. The amounts of HSi(OMe)$_3$ and Si(OMe)$_4$ formed at that point were essentially equal in both the control (Example 1C) and H$_2$-activation (Example 4) experiments. However, the rate of the hydrogen-activated reaction was approximately 13% higher. This rate improvement was evident from the outset of the reaction.

TABLE 8

EFFECT OF H$_2$ ACTIVATION ON HSi(OMe)$_3$ DIRECT SYNTHESIS IN THERMINOL ® 59

| EX- AMPLE | Si CONV., % | RATE, % Si/hr | HSi(OCH$_3$)$_3$, kg | Si(OCH$_3$)$_4$, kg | SEL |
|---|---|---|---|---|---|
| 1C: CONTROL | 85 | 3.75 | 3.54 | 0.13 | 27.23 |
| | 87.7 | 3.64 | 3.63 | 0.14 | 25.93 |
| 4: 1803.9 L H$_2$ | 85 | 4.25 | 3.56 | 0.11 | 32.36 |
| | 93.7 | 3.76 | 3.93 | 0.13 | 30.23 |

Selectivities in the control (Example 1C) and the hydrogen-activated reaction (Example 4) were close up until ~65% Si conversion. Beyond that point, selectivity in the control reaction declined steadily. With H$_2$ activation, selectivity decline occurred after >80% Si conversion. Acceptable rates and selectivities were sustainable up to ~94% Si conversion, whereas the control had to be terminated at ~88% Si conversion. This additional stability afforded ~8% higher HSi(OMe)$_3$ yield from the H$_2$-activation experiment. Methane formation is typically low when Therminol® 59 is the solvent. It was reduced to unobservable levels for almost the entire duration of the H$_2$-activation experiments. Thus, significant and advantageous improvements in reaction rate, selectivity and stability were realized when hydrogen activated silicon-copper (II) hydroxide mixtures were reacted with methanol in THERMINOL® 59.

Example 5

This Example illustrates the continuation of a hydrogen-activated batchwise experiment to a second batch of silicon containing no additional copper catalyst. Two experiments, one in NALKYLENE® 550BL and the other in THERMINOL® 59, are described.

Both reactions were performed according to the general procedure above using a methanol flow rate of 5 g/min. 1438 L H$_2$ were used to activate the reaction slurry in NALKYLENE® 550BL (Example 5A) and 1080 L H$_2$ for the experiment in THERMINOL® 59 (Example 5B). After approximately 70 percent of the silicon had been converted in each experiment, the reactor was cooled to room temperature and silicon was added to it pneumatically with nitrogen to minimize exposure of the reaction mixture to the air. Thereafter, the reactor was heated to 250° C. and the methanol flow reinitiated at 5 g/min. Reactions were terminated when at least 25% of the second silicon charge had been reacted.

Table 9 sets forth the data for the two experiments of this Example. It is clear that the added silicon was activated by the copper already present in the reactor to produce HSi(OMe)$_3$ at acceptable rates and selectivities. Thus, another advantage of the hydrogen activation process of the present invention is that it can be carried out in semicontinuous or continuous operation, wherein an initial charge of silicon and copper catalyst is activated with a reducing agent such as hydrogen and partially reacted with alcohol. Subsequently, silicon, without additional copper catalyst, is added to the reactor periodically and the Direct Synthesis is continued. In this manner, there is no buildup of copper in the reactor over numerous silicon conversion cycles. High copper concentrations favor side reactions such as alcohol reduction and alkylsilicate formation.

TABLE 9

CONTINUITY OF H$_2$-ACTIVATED HSi(OMe)$_3$ DIRECT SYNTHESIS IN NALKYLENE ® 550 BL AND THERMINOL ® 59 AT 250° C., 900 RPM

| EXAMPLE | Si CONV., % | RATE, % Si/hr | HSi(OCH$_3$)$_3$, kg | Si(OCH$_3$)$_4$, kg |
|---|---|---|---|---|
| 5A | | | | |
| First Charge | 72 | 6.13 | 2.94 | 0.21 |
| After 700 g Si | 54 | 6.60 | 2.21 | 0.20 |
| OVERALL | 126 | 6.33 | 5.15 | 0.41 |
| 5B | | | | |
| First Charge | 70.8 | 5.95 | 3.09 | 0.10 |
| After 1 kg Si | 82.7 | 5.12 | 3.39 | 0.28 |
| OVERALL | 153.5 | 5.47 | 6.48 | 0.38 |

Example 6

This Example illustrates the Direct Synthesis of HSi(OC$_2$H$_5$)$_3$ in the polyaromatic hydrocarbon solvent, MARLOTHERM® S, from hydrogenated copper (II) hydroxide-silicon mixtures and ethanol. The hydrogen activated slurry was initially reacted with methanol before the reaction was continued with ethanol.

The experiment was conducted with 1 kg silicon (Si-2), 7.05 g copper (II) hydroxide catalyst, 0.8 g FS 1265 and 2.1 kg MARLOTHERM® S. The slurry was activated with hydrogen as described in the general procedure above. A total of 1213.3 L H$_2$ was introduced between 150°–250° C. over a period of 65 minutes. With the temperature at 250° C., methanol was introduced at 4.3 g/min and its flow maintained for 5 hours. In that time, ~20% silicon was converted primarily to HSi(OCH$_3$)$_3$ and Si(OCH$_3$)$_4$.

After the reactor temperature had been lowered and stabilized at 230° C., ethanol was introduced at 4.3 g/min. Nitrogen flow was maintained during the temperature drop. No H$_2$ was present in the vent gas just prior to the start of the ethanol feed. Vent gas analysis 5 minutes after the initiation of ethanol flow showed the presence of H$_2$. Hydrogen content in the vent gas stabilized after about 30 minutes. The liquid reaction product was analyzed periodically for HSi(OC$_2$H$_5$)$_3$, Si(OC$_2$H$_5$)$_4$ and other byproducts. The product contained ~80 wt % HSi(OC$_2$H$_5$)$_3$, ~20 wt % C$_2$H$_5$OH and a trace of Si(OC$_2$H$_5$)$_4$.

Example 7

This Example illustrates the Direct Synthesis of HSi(OCH$_3$)$_3$ in the alkylated benzene solvent, NALKYLENE® 550BL, following reductive activation of the Cu(OH)$_2$-silicon mixture with THERMINOL® 59.

The reductive activation step of the experiment was conducted by preparing a slurry of 7.05 g Cu(OH)$_2$ in 1002.6 kg THERMINOL® 59 in the Chemineer® reactor described above and heating it to 250° C. in the presence of nitrogen. This temperature was maintained for 30 minutes before the heater was turned off and the slurry allowed to cool (3 hr) to ambient temperature (~23° C.). Stirring was discontinued to allow the suspended solids in the reactor to settle over the ensuing 2 hr. The reactor was then opened and the THERMINOL® 59 carefully siphoned away from the settled reddish brown solids. A total of 1 kg THERMINOL® 59 was recovered. NALKYLENE® 550BL (2 kg), FS 1265 (0.6 g) and silicon Si-1 (1 kg) were then added to the reactor and the Direct Synthesis was performed at 250° C. with a methanol flow of 3.3 g/min.

Reaction was continued for 21.7 hr and in that time 80.8 weight percent of the silicon was converted to 4.1 kg reaction product containing 3.29 kg HSi(OCH$_3$)$_3$ and 0.23 kg Si(OCH$_3$)$_4$. Overall, selectivity was 14.6 over the course of the Direct Synthesis Between 30–50% silicon conversion, HSi(OCH$_3$)$_3$ declined from ~90 wt % to ~80 wt %, Si(OCH$_3$)$_4$ from <3 wt % to ~10 wt % of the crude reaction product. CH$_4$ increased to a maximum of 7 volume % of the effluent gas. Thus, there was a performance improvement over the control reaction (Example 1B) with Cu(OH)$_2$ in NALKYLENE® 550BL at the same methanol feed rate and reaction temperature. In the control, HSi(OCH$_3$)$_3$ dropped to ∞70 wt %, Si(OCH$_3$)$_4$ increased to ~25 wt % and CH$_4$ rose to ~14 volume % during the unstable period. The post-reaction slurry contained 0.79 wt % Si compared to 0.87 wt % Si in Example 1B.

What is claimed is:

1. A process for producing trialkoxysilane of the formula HSi(OR)$_3$ wherein R is an alkyl group containing 1 to 6 carbon atoms inclusive, comprising (a) slurrying silicon metal in a thermally stable solvent in the presence of a catalyst precursor which is halogen-free and which comprises copper at least part of which is not in the Cu° state and is reducible to the Cu° state, (b) fully reducing said copper which is not in the Cu° state to the Cu° state, thereby generating a catalyst for the reaction of step (c), and (c) reacting said silicon metal with an alcohol of the formula ROH in the presence of the catalyst generated in step (b) to form said trialkoxysilane.

2. The process of claim 1 wherein R is methyl.

3. The process of claim 1 wherein R is ethyl.

4. The process of claim 1 wherein said catalyst precursor comprises one or more copper(I) compounds.

5. The process of claim 1 wherein said catalyst precursor comprises one or more copper(II) compounds.

6. The process of claim 1 wherein said catalyst precursor comprises copper(II) hydroxide.

7. The process of claim 1 wherein step (b) is carried out by reacting said catalyst precursor with gaseous hydrogen.

8. The process of claim 1 wherein step (b) is carried out by reacting said catalyst precursor with carbon monoxide.

9. The process of claim 1 wherein step (b) is carried out by reacting said catalyst precursor with SiH$_4$.

10. The process of claim 1 wherein step (b) is carried out by reacting said catalyst precursor with an organosilane containing one or more SiH groups.

11. The process of claim 1 wherein step (b) is carried out by reacting said catalyst precursor with an organosilane containing one or more SiH$_2$ groups.

12. The process of claim 1 wherein step (b) is carried out by reacting said catalyst precursor with an organosilane containing one or more SiH$_3$ groups.

13. The process of claim 1 wherein the slurry formed in step (a) contains alcohol of the formula ROH.

14. The process of claim 1 wherein hydrogen is formed in the reaction of step (c) and all or a portion of said hydrogen is recycled to step (b) and is used in the reduction of step (b).

15. The process of claim 1 wherein in step (a) said solvent comprises polyaromatic hydrocarbons, and said catalyst precursor is reduced in step (b) by heating in said solvent, and said step (c) is carried out in a solvent comprising alkylated benzene.

* * * * *

UNITED STATES PATENT AND TRADEMARK OFFICE
CERTIFICATE OF CORRECTION

PATENT NO. : 5,728,858
DATED : March 17, 1998
INVENTOR(S) : Kenrick M. Lewis, et al.

It is certified that error appears in the above-identified patent and that said Letters Patent is hereby corrected as shown below:

Column 5, line 1: "R\' " should read --R' --

Column 14, line 20: "contains" should read --columns--

Column 16, line 14: "Cl" should read --Cl$^-$ --

Column 18, line 20: "mole which" should read --mole %, which--

Column 21, line 23: "(1I)" should read --(II)--

Column 22, line 15: " $\infty$ 70 wt%" should read -- $\sim$ 70 wt% --

Signed and Sealed this

Tenth Day of November 1998

Attest:

BRUCE LEHMAN

Attesting Officer     Commissioner of Patents and Trademarks